US008298517B2

(12) United States Patent
Horstman et al.

(10) Patent No.: US 8,298,517 B2
(45) Date of Patent: Oct. 30, 2012

(54) PERSONAL CARE COMPOSITIONS HAVING IMPROVED COMPATIBILITY AND PROVIDING IMPROVED SUN PROTECTION

(75) Inventors: John Bernard Horstman, Midland, MI (US); Douglas W. King, Midland, MI (US); Paul W. Pretzer, Midland, MI (US); Randall Schmidt, Midland, MI (US); Gary Wieber, Midland, MI (US); Tina Leaym, Saginaw, MI (US); Maria R. Pretzer, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 12/993,867

(22) PCT Filed: Jul. 6, 2009

(86) PCT No.: PCT/US2009/049662

§ 371 (c)(1), (2), (4) Date: Nov. 22, 2010

(87) PCT Pub. No.: WO2010/014352

PCT Pub. Date: Feb. 4, 2010

(65) Prior Publication Data

US 2011/0110873 A1 May 12, 2011

Related U.S. Application Data

(60) Provisional application No. 61/083,189, filed on Jul. 24, 2008, provisional application No. 61/084,635, filed on Jul. 30, 2008.

(51) Int. Cl.

| | |
|---|---|
| ***A61Q 1/02*** | (2006.01) |
| ***A61Q 5/00*** | (2006.01) |
| ***A61Q 11/00*** | (2006.01) |
| ***A61Q 15/00*** | (2006.01) |
| ***A61Q 17/04*** | (2006.01) |
| ***A61Q 19/02*** | (2006.01) |

(52) U.S. Cl. ............ 424/59; 424/401; 424/485; 424/62; 424/65; 424/70.9; 424/70.121; 424/94.1; 514/772

(58) Field of Classification Search ........................ None
See application file for complete search history.

(56) References Cited

U.S. PATENT DOCUMENTS

| | | | | |
|---|---|---|---|---|
| 2,410,346 | A | 10/1946 | Hyde | |
| 4,122,029 | A | 10/1978 | Gee et al. | |
| 4,289,891 | A | 9/1981 | Brown, Jr. | |
| 5,387,417 | A | 2/1995 | Rentsch | |
| 5,557,000 | A | 9/1996 | Minemura | |
| 5,811,487 | A | 9/1998 | Schulz, Jr. et al. | |
| 6,825,264 | B2 | 11/2004 | Oda et al. | |
| 2001/0044484 | A1 | 11/2001 | Hatanaka et al. | |
| 2003/0109660 | A1 * | 6/2003 | Oda et al. | 528/14 |
| 2003/0124073 | A1 * | 7/2003 | Wyatt et al. | 424/61 |
| 2007/0132113 | A1 | 6/2007 | Hinterman | |
| 2007/0148115 | A1 | 6/2007 | Cook et al. | |
| 2011/0262375 | A1 | 10/2011 | Hinterman et al. | |

FOREIGN PATENT DOCUMENTS

| | | | |
|---|---|---|---|
| EP | 1062944 | B1 | 3/2004 |
| GB | 783867 | | 10/1957 |
| WO | WO 2005/075542 | A1 * | 8/2005 |
| WO | 2009071662 | A2 | 6/2009 |

OTHER PUBLICATIONS

Petrarch Catalog 2000 "Silanes, Silicones and Homogeneous Catalysts" p. 250-256.*

Kowandy, Veronique,et al., "Bodied MQ-T Propyl Silicone Resins in Color Cosmetic Applications," IP.com Prior Art Database Journal, Dec. 4, 2008, pp. 1-15, West Henrietta, NY, US.

Caprasse, Virginie, et. al., "A New Silicone Resin for Personal Care Applications," Research Disclosure, Oct. 1, 2004, vol. 486, No. 8., Mason Publications, Hamshire, GB.

* cited by examiner

*Primary Examiner* — Richard Schnizer
*Assistant Examiner* — Alma Pipic
(74) *Attorney, Agent, or Firm* — Alan Zombeck; Catherine U. Brown

(57) ABSTRACT

Personal care composition having improved compatibility and providing improved sun protection are obtained by including a liquid silicone resin having greater than 50 mole percent $Me_3SiO_{1/2}$ and $PrSiC_{3/2}$ units, where Me is methyl and Pr is propyl in the composition. If desired to enable additional compatibility of ingredients comprising the personal care composition, the liquid silicone resin can also contain $PhSiO_{3/2}$ or $Ph2SiO_{2/2}$ units, where Ph is phenyl, or a mixture thereof.

8 Claims, No Drawings

PERSONAL CARE COMPOSITIONS HAVING IMPROVED COMPATIBILITY AND PROVIDING IMPROVED SUN PROTECTION

CROSS REFERENCE TO RELATED APPLICATIONS

This application is a U.S. national stage filing under 35 U.S.C. §371 of PCT Application No. PCT/US09/49662 filed on 6 Jul. 2009, currently pending, which claims the benefit of U.S. Provisional Patent Application No. 61/083,189 filed 24 Jul. 2008 and U.S. Provisional Patent Application No. 61/084,635 filed 30 Jul. 2008 under 35 U.S.C. §119 (e). PCT Application No. PCT/US09/49662 and U.S. Provisional Patent Application Nos. 61/083,189 and 61/084,635 are hereby incorporated by reference.

FIELD OF THE INVENTION

Personal care compositions having improved compatibility and providing improved sun protection are obtained by including a liquid silicone resin having greater than 50 mole percent $Me_3SiO_{1/2}$ and $PrSiO_{3/2}$ units, where Me is methyl and Pr is propyl in the composition. If desired to enable additional compatibility of select ingredients comprising the personal care composition, the liquid silicone resin can also contain $PhSiO_{3/2}$ or $Ph_2SiO_{2/2}$ units, where Ph is phenyl, or a mixture thereof.

SUMMARY OF THE INVENTION

Consumers are increasingly aware of the link between ultraviolet (UV) exposure and skin cancer, and a desire to slow the visual effects of aging is a primary factor in the surge of products designed to protect the skin. In this invention, we have discovered that liquid silicone resins comprising $Me_3SiO_{1/2}$ and $PrSiO_{3/2}$ units, where Me is methyl and Pr is propyl, unexpectedly boost the sun protection factor (SPF) of a standard lotion (2% Sepigel 305) containing ultraviolet absorbers by as much as 750%.

Personal Care products typically are made up of mixtures of multiple components. When adding new components to a personal care formulation to perform a specific function, the formulator is often faced with compatibility issues with the other components. Potential ingredients that have broad compatibility with standard components and can help compatibilize multiple components enable valued formulating flexibility. The liquid silicone resins of the present invention have been found to enable single phase compatibility of two ingredients that are incompatible when used by themselves. The liquid silicone resins are especially well suited for compatibilizing linear or cyclic silicones with other organic personal care ingredients.

In addition, these liquid silicone resins exhibit compatibility with a broad range of personal care formulating ingredients and their compatibility can be extended to a wider range of ingredients by incorporating up to 50 mole percent % of $PhSiO_{3/2}$ or $Ph_2SiO_{2/2}$ units, where Ph is phenyl. This broad compatibility allows utility of these liquid silicone resins in a wide range of personal care formulations (e.g. formulations additionally including cosmetic ingredients).

Formulators are always looking for easier ways to deliver personal care ingredients. Providing the silicone resin in a liquid form allows for easy delivery of the component to the formulation and the lower molecular weight that typically accompanies liquid resins (compared to solid analogues) is entropically favored for enhanced compatibility.

This invention relates to a personal care composition comprising 0.1 to 40 weight percent based on the total weight of the personal care composition of a liquid silicone resin comprising the units:

$$(PrSiO_{3/2})_m$$

$$(Me_3SiO_{1/2})_n$$

$$(PhSiO_{3/2})_o$$

$$(Ph_2SiO_{2/2})_p$$

where Pr is propyl, Me is methyl, and Ph is phenyl, m is 0.05 to 0.80, n is 0.75 to 0.20, o is 0 to 0.35, p is 0 to 0.35, m+n is from greater than 0.5 to 1, o+p is 0 to 0.5, n/(m+n+o+p) is at least 0.2, and m+n+o+p is 0.9 to 1.

DETAILED DESCRIPTION OF THE INVENTION

The liquid silicone resin useful in the personal care compositions of the present invention comprise the units:

$$(PrSiO_{3/2})_m$$

$$(Me_3SiO_{1/2})_n$$

$$(PhSiO_{3/2})_o$$

$$(Ph_2SiO_{2/2})_p$$

where Pr is propyl, Me is methyl, and Ph is phenyl, m is 0.05 to 0.80, n is 0.75 to 0.20, o is 0 to 0.35, p is 0 to 0.35, m+n is from greater than 0.5 to 1, o+p is 0 to 0.5, n/(m+n+o+p) is at least 0.2, and m+n+o+p is 0.9 to 1. Generally, the liquid silicone resin is added to the personal care composition in an amount from 0.1 to 40 weight percent based on the total weight of the personal care composition. Alternatively, the liquid silicone resin is added to personal care composition in an amount from 1 to 25 weight percent based on the total weight of the personal care composition. Alternatively, the liquid silicone resin is added to personal care compositions in amount from 1 to 10 weight percent on the same basis. Generally, m is 0.05 to 0.80, alternatively 0.05 to 0.7, alternatively 0.09 to 0.5. Generally, n is 0.75 to 0.20, alternatively 0.65 to 0.25, alternatively 0.6 to 0.3. Generally, m+n is from greater than 0.5 to 1, alternatively m+n is 0.6 to 1, alternatively m+n is 0.7 to 1, alternatively m+n is 0.7 to 0.9.

It is often useful with personal care compositions to be able to tune the compatibility of the various ingredients. Liquid silicone resins containing $PrSiO_{3/2}$ units exhibit compatibility with a broad range of personal care formulating ingredients and their compatibility can be extended to a wider range of ingredients by also incorporating into the liquid silicone resin $(PhSiO_{3/2})_o$ units, $(Ph_2SiO_{2/2})_p$ units, or a mixture thereof, where Ph is phenyl. Generally in the liquid silicone resins useful in the present invention, o is 0 to 0.35, alternatively 0.05 to 0.25, alternatively 0.10 to 0.20. Generally, p is 0 to 0.35, alternatively 0.05 to 0.30, alternatively 0.10 to 0.25. Generally, o+p is 0 to 0.5, alternatively 0 to 0.40, alternatively 0 to 0.30, alternatively 0.1 to 0.30.

To ensure the silicone resin is liquid at room temperature (25° C.), the resin should contain a sufficient molar percentage of $(Me_3SiO_{1/2})_n$ units since these units effectively end cap the structure limiting molecular growth. The end cap units $(Me_3SiO_{1/2})_n$ should be present in a molar quantity such that the molar quantity $(Me_3SiO_{1/2})$ units divided by the total moles of resin building units is at least 0.2. In other words, n/(m+n+o+p) is at least 0.2, alternatively n/(m+n+o+p) is at least 0.3, alternatively n/(m+n+o+p) is at least 0.4

The liquid silicone resins useful in the present invention may also contain up to 10 mole percent of other silicone building blocks (M, D, T and Q units) without substantially altering the invention. Therefore, m+n+o+p is 0.9 to 1, alternatively m+n+o+p is 0.95 to 1, alternatively m+n+o+p=1.

The viscosity of the liquid silicone resin generally is less than 100,000 $mm^2/s$, alternatively less than 10,000 $mm^2/s$, alternatively 10 to 5000 $mm^2/s$, alternatively 20 to 250 $mm^2/s$.

Silicone resins are well known in the art and are typically prepared by co-hydrolyzing and condensing organosilanes having one to four hydrolyzable groups on the silicon atom, such as a halogen or alkoxy group. Thus, the liquid silicone resin useful in the present invention can be obtained by co-hydrolyzing propyltrimethoxysilane, propyltriethoxysilane, propyltripropoxysilane with trimethylmethoxysilane, trimethylethoxysilane or by co-hydrolyzing the aforementioned propylalkoxysilanes with various phenyl-containing alkoxysilanes. Examples of these alkoxysilanes include diphenyldimethoxysilane, diphenyldiethoxysilane, phenyltrimethoxysilane and phenyltriethoxysilane. Propyltrichlorosilane can also be hydrolyzed alone, or in the presence of alcohol. In this case, co-hydrolyzation can be carried out by adding trimethylchlorosilane, phenyltrichlorosilane, and diphenyldichlorosilane or similar chlorosilanes and methyltrimethoxysilane, methyltriethoxysilane, methyltriisopropoxysilane, or similar methylalkoxysilanes. Alcohols suitable for these purposes include methanol, ethanol, n-propyl alcohol, isopropyl alcohol, butanol, methoxy ethanol, ethoxy ethanol, or similar alcohols. Examples of hydrocarbon-type solvents which can also be concurrently used include toluene, xylene, or similar aromatic hydrocarbons; hexane, heptane, isooctane, or similar linear or partially branched saturated hydrocarbons; and cyclohexane, isododecane, or similar aliphatic hydrocarbons.

The present invention also relates to a personal care composition suitable for application to the skin, hair, lips, lashes and nails, the improvement comprising the incorporation of from 0.1 to 40 weight percent based on the total weight of the personal care composition of a liquid silicone resin comprising the units:

$(PrSiO_{3/2})_m$ $(Me_3SiO_{1/2})_n$ $(PhSiO_{3/2})_o$ $(Ph_2SiO_{2/2})_p$ where Pr is propyl, Me is methyl, and Ph is phenyl, and m, n, o, p, m+n, o+p, n/(m+n+o+p), and m+n+o+p are as defined above.

The personal care composition in accordance with the present invention may take any form. Alternatively, the personal care composition is in the form of an ointment, wipes, cream, gel, paste, foam, aerosol, gelled stick, wax-based stick, solution or liquid suspension.

The personal care composition in accordance with the present invention may comprise any ingredient listed in the CTFA INCI dictionary. Alternatively, the personal care composition may comprise at least one of the following active ingredients: optional cosmetic active or a health care active such as an anti-acne agent, anti-caries agent, antidandruff agent, antifungal agent, antimicrobial agent, antioxidant, antiperspirant agent, cosmetic biocide, deodorant agent, external analgesic, oral care agent, oral care drug, oxidizing agent, reducing agent, skin bleaching agent, skin protectant, sunscreen agent (UV light absorbing or light reflecting agent), pigments, moisturizers, vitamins, enzymes, optical brighteners, or surfactants.

The liquid silicone resin is used in any form but mainly as part of cosmetic compositions which can be in the form of dispersions and emulsions, solid or liquid. These liquid silicone resins are useful in a number of different products, including hair care products such as hairsprays, shampoos, shower gels, mousses, styling gels, hair relaxers, and lotions, cream rinses/conditioners, hair tonics, hair dyes and colorants, permanent waves and bleaches. Also included are skin care products such as cleansers, moisturizers, conditioners, lipsticks, eye makeup, foundations, fingernail polish, suntan products, sunscreen products, facial treaments, pre-shave products, aftershave products, color cosmetics, mascaras, eyeliners, powders, antiperspirant/deodorant products and depilatories.

The personal care composition according to the invention may also contain a number of optional ingredients:

(i) non-volatile polysiloxane having the structure:

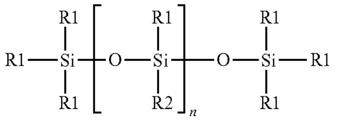

wherein n has a value sufficient to provide polysiloxane polymers having a viscosity in the range of 10-10,000 $mm^2/s$. R1 and R2 can be alkyl radicals containing 1-20 carbon atoms or aryl groups, alternatively alkyl radicals containing 1-6 carbon atoms, alternatively methyl or phenyl groups. Typically, the value of n is 20-500, alternatively 80-375. Some illustrative polysiloxane polymers include polydimethylsiloxane, polydiethylsiloxane, polymethylethylsiloxane, polymethylphenylsiloxane, and polydiphenylsiloxane;

(ii) Alkylmethylsiloxanes: These siloxane polymers generally will have the formula $Me_3SiO[Me_2SiO]_a[MeRSiO]_bSiMe_3$, in which R is a hydrocarbon group containing 6-30 carbon atoms, Me represents methyl, and the degree of polymerization (DP), i.e., the sum of a and b is 3-50. Both the volatile and liquid species of alkymethysiloxanes can be used in the composition.

(iii) Silicone gums: Polydiorganosiloxane gums are known in the art and are available commercially. They consist of generally insoluble polydiorganosiloxanes having a viscosity in excess of 1,000,000 centistoke ($mm^2/s$) at 25° C., alternatively greater than 5,000,000 centistoke ($mm^2/s$) at 25° C. These silicone gums are typically sold as compositions already dispersed in a suitable solvent to facilitate their handling. Ultra-high viscosity silicones can also be included as optional ingredients. These ultra-high viscosity silicones typically have a kinematic viscosity greater than 5 million centistoke ($mm^2/s$) at 25° C., to about 20 million centistoke ($mm^2/s$) at 25° C. Compositions of this type in the form of suspensions are most preferred, and are described for example in U.S. Pat. No. 6,013,682.

(iv) Silicone polyamides: Representative compositions of suitable silicone polyamide copolymers are set forth in detail in U.S. Pat. No. 5,981,680.

(v) Solid Silicone resins: These resin compositions are generally highly cross-linked polymeric siloxanes. Branching is obtained by incorporating trifunctional and/or tetrafunctional silanes with the monofunctional silane and/or difunctional silane monomers used during manufacture. The degree of branching required to obtain a suitable silicone resin will vary according to the specifics of the silane monomer units incorporated during manufacture of the silicone resin. In general, any silicone having a sufficient level of trifunctional and tetrafunctional siloxane monomer units, and hence possessing sufficient levels of branching to dry down to a rigid or a hard film can be considered to be suitable for use as the silicone resin. Commercially available silicone resins suitable for applications herein are generally supplied in an unhardened form in low viscosity volatile or nonvolatile silicone fluids or alternatively as a solid flake. The silicone resins should be incorporated into compositions of the invention in their non-hardened forms rather than as hardened resinous structures.

(vi) Silicone elastomers: Such elastomers are generally reaction products obtained by combining an organopolysiloxane having an unsaturated group bound to a terminal silicon atom and an organohydrogensiloxane, and then subjecting it to at least a partial cure. Some examples of suitable elastomers are compositions known in the cosmetic industry under their INCI name of Dimethicone/Vinyl Dimethicone Crosspolymer, Dimethicone Crosspolymer, Dimethicone/Bis-Isobutyl PPG-20 Crosspolymer, Dimethicone/PPG-20 Crosspolymer, Bis-Vinyldimethicone/Bis-Isobutyl PPG-20 Crosspolymer, Bis-Vinyldimethicone/PPG-20 Crosspolymer, Polysilicone-11, Vinyl Dimethicone/Lauryl Dimethicone Crosspolymer, Trifluoropropyl Dimethicone/PEG-10 Crosspolymer, Lauryl Dimethicone/Polyglycerin-3 Crosspolymer, Dimethicone/Phenyl Vinyl Dimethicone Crosspolymer, Dimethicone/PEG-10 Crosspolymer, PEG-15/Lauryl Dimethicone Crosspolymer, and PEG-10/Lauryl Dimethicone Crosspolymer. Emulsions and suspension of these polysiloxane elastomers can also be used as components of the composition. Polysiloxane elastomers in the form of powders coated with different organic and inorganic materials such as mica and silica can also be used.

(vii) Carbinol Fluid: These materials are described in WO 03/101412 A2, and can be commonly described as substituted hydrocarbyl functional siloxane fluids or resins.

(viii) Water soluble or water dispersible silicone compositions: These are also known as polyalkylene oxide silicone copolymers, silicone poly(oxyalkylene) copolymers, silicone glycol copolymers, or silicone surfactants. These can be linear rake or graft type materials, or ABA type where the B is the siloxane polymer block, and the A is the poly(oxyalkylene) group or ABn type where A is the poly(oxyalkylene) and B the siloxane polymer block. The poly(oxyalkylene) group can consist of polyethylene oxide, polypropylene oxide, or mixed polyethylene oxide/polypropylene oxide groups. Other oxides, such as butylene oxide or phenylene oxide are also possible.

(ix) Aminosiloxanes such as Dow Corning® 2-2078 Fluid and Dow Corning® Q2-8220 Conditioning Additive.

Compositions according to the invention can be in the form of water/oil (w/o) or water/solvent (w/s) emulsions using silicone emulsifiers. It is preferred that this water-in-silicone emulsifier is non-ionic. Alternatively, the water-in-silicone emulsifier is selected from polyoxyalkylene-substituted silicones, silicone alkanolamides, silicone esters and silicone glycosides. Suitable silicone-based surfactants are well known in the art, and have been described for example in U.S. Pat. No. 4,122,029, U.S. Pat. No. 5,387,417, and U.S. Pat. No. 5,811,487 and include polydiorganosiloxane polyoxalkylene copolymers containing at least one polydiorganosiloxane segment consisting essentially of $R_c SiO_{(4-c)/2}$ siloxane units wherein c has a value of from 0 to 3, inclusive, there being an average value of approximately 2 R groups per silicon for all siloxane units in the copolymer, and R denotes a radical selected from the group consisting of methyl, ethyl, vinyl, phenyl, and a divalent radical bonding a polyoxyalkylene segment to the polydiorganosiloxane segment, at least 95 percent of all R being methyl; and at least one polyoxyalkylene segment having an average molecular weight of at least 1000 and consisting of from 0 to 50 mol percent polyoxypropylene units and from 50 to 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from 2 to 8. Alternatively, the silicone-based surfactant can be a cross-linked emulsifier in which at least two organopolysiloxane-polyoxyalkylene molecules are cross-linked by a cross-linking radical; the cross-linked organopolysiloxane-polyoxyalkylene emulsifier having the formula:

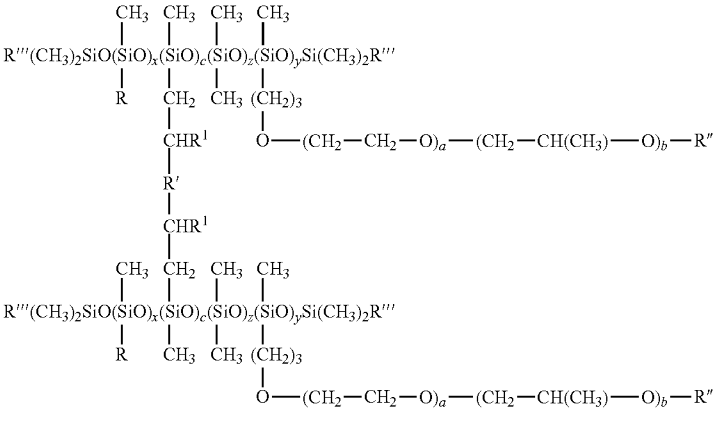

wherein R is an aliphatic radical having 2 to 25 carbon atoms; R' is an organic or organosiloxane group which does not contain hydrolysable bonds; R" is a terminal group; R''' is independently an aliphatic radical having 1 to 25 carbon atoms; $R^1$ is independently selected from the group consisting of hydrogen and an aliphatic radical containing 1-3 carbon atoms; x is an integer from 0 to 100; c is an integer from 1 to 5; z is an integer from 0 to 600; y is an integer from 1 to 10; x+y+z>40; a is an integer from 4 to 40; b is an integer from 0 to 40; a/b>1. The amount of the silicone emulsifying agent in the final composition may vary widely, but typically would be from 0.05% to 1.5%, alternatively 0.1 to 1%, alternatively 0.15 to 0.8% by weight, alternatively 0.2 to 0.6% by weight.

Other useful optional components can be included in the compositions according to the invention, such as fragrances, preservatives, vitamins and their derivatives, whitening agents, anti-oxidants, ceramides, amino-acid derivatives, liposomes, polyols, such as glycerine and propylene glycol and botanicals (plant extracts) conditioning agents for hair and skin such as quaternary polymers or silicone materials such as aminofunctional silicones.

Other additives can include, depending on the use, sunscreen agents, humectants, preservatives such as parabens, emollients, occlusive agents, and esters, anti-acne agents, antidandruff agents, antimicrobial agents, antifungal agents, antiviral agents, antioxidants, antiperspirant agents and deodorant agents, cosmetic biocides, oxidizing agents, reducing agents, skin bleaching agents, skin protectants, insect repellents, and surfactants, cleansing agents such as anionic detersive surfactant, foam boosting agents, agents for artificially tanning and/or browning the skin (self-tanning agents), such as, for example, dihydroxyacetone (DHA), electrolytes, pH control agents, oxidative and non oxidative hair colorants, fixative resins, film formers, powders, pigments and glittering agents.

The composition according to the invention can also be in the form of aerosols in combination with propellant gases, such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether.

The composition according to the invention can also be in the form of rinse off applications such as shower gels, shampoos and rinse off conditioners and can include the following ingredients such as skin and hair conditioning agents, including but not limited to Polyquaternium-7, Polyquaternium-8, Polyquaternium-10, Polyquaternium-11, and Polyquaternium-23. The above cationic organic polymers and others are described in more details in U.S. Pat. No. 4,240,450 which is hereby incorporated by reference to further describe the cationic organic polymers. Other categories of conditioners may also be employed in the compositions as a cationic conditioning agent. These include cationic surfactants such as cetyl trimethylammonium chloride, cetyl trimethylammonium bromide, and stearyltrimethylammonium chloride.

The personal care composition of the present invention can also include cleansing agents including but not limited to well-known anionic detersive surfactants typically used in shampoo formulations. The anionic detersive surfactants are exemplified by sulfonated glyceryl esters of fatty acids, amides of amino sulfonic acids such as the sodium salt of oleyl methyl tauride, alkali metal alkyl sulfates such as sodium lauryl sulfate, ammonium lauryl sulfate or triethanol amine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms. The anionic detersive surfactant is present in the shampoo compositions of this invention in an amount from about 5 to 50 wt % and alternatively about 5 to 25 wt % based on the total weight of the composition.

The personal care composition of the present invention can also include foam boosting agents alternatively selected from the group consisting of fatty acid alkanolamides and amine oxides. The fatty acid alkanolamides are exemplified by isostearic acid diethanolamide, lauric acid diethanolamide, capric acid diethanolamide, coconut fatty acid diethanolamide, linoleic acid diethanolamide, myristic acid diethanolamide, oleic acid diethanolamide, stearic acid diethanolamide, coconut fatty acid monoethanolamide, oleic acid monoisopropanolamide, and lauric acid monoisopropanolamide. The amine oxides are exemplified by N-cocodimethylamine oxide, N-lauryl dimethylamine oxide, N-myristyl dimethylamine oxide, N-stearyl dimethylamine oxide, N-cocamidopropyl dimethylamine oxide, N-tallowamidopropyl dimethylamine oxide, bis(2-hydroxyethyl) C12-15 alkoxypropylamine oxide. Alternatively a foam booster is selected from the group consisting of lauric acid diethanolamide, N-lauryl dimethylamine oxide, coconut acid diethanolamide, myristic acid diethanolamide, and oleic acid diethanolamide. The foam boosting agent is alternatively present in the shampoo compositions of this invention in an amount from about 1 to 15 wt % and more alternatively about 2 to 10 wt % based on the total weight of the composition. The composition may further comprise a polyalkylene glycol to improve lather performance. Concentration of the polyalkylene glycol in the shampoo composition may range from about 0.01% to about 5%, alternatively from about 0.05% to about 3%, alternatively from about 0.1% to about 2%, by weight of the composition.

The personal care composition according to the invention can include a sunscreen as an optional or as a main ingredient. Sunscreens include but are not limited to those components which absorb ultraviolet light between 290 and 320 nanometers, i.e., the UV-B region, such as para-aminobenzoic acid derivatives and cinnamates derivatives such as ethyl hexyl methoxy cinnamate; and those compositions which absorb ultraviolet light in the range of 320 to 400 nanometer, i.e., the UV-A region, such as benzophenone derivatives and butyl methoxy dibenzoylmethane derivatives, and hydrophilic compositions such as terephthalylidene dicamphor sulfonic acid and benzylidine-2-camphor sulphonic acid derivatives. Non-limiting examples of suitable oil-soluble sunscreens are disclosed in The Cosmetic, Toiletry, and Fragrance Association's The International Cosmetic Ingredient Dictionary and Handbook, 10th Ed., Gottschalck, T. E. and McEwen, Jr., Eds. (2004), p. 2267 and pp. 2292-93 and include benzophenone-3, bis-ethylhexyloxyphenol methoxyphenyl triazine, butyl methoxydibenzoyl-methane, diethylamino hydroxybenzoyl hexyl benzoate, drometrizole trisiloxane, ethylhexyl methoxy-cinnamate, ethylhexyl salicylate, ethylhexyl triazone, octocrylene, homosalate, polysilicone-15, and derivatives and mixtures thereof. Non-limiting examples of suitable oil-insoluble sunscreens include methylene bis-benzotriazolyl tetramethylbutylphenol, titanium dioxide, zinc cerium oxide, zinc oxide, and derivatives and mixtures thereof. It is to be understood that "oil-insoluble sunscreen" does not encompass water-soluble sunscreens. Non-limiting examples of water-soluble sunscreens include phenylbenzimidazole and disodium phenyl dibenzimidazole tetrasulfonate.

The personal care compositions according to the invention can also contain pigments or alternatively nanopigments (average primary particle size: generally between 5 nm and 100 nm, alternatively between 10 and 50 nm) of coated or uncoated metal oxides, such as, for example, nanopigments of titanium oxide (amorphous or crystallized in rutile and/or anatase form), of iron oxide, of zinc oxide, of zirconium oxide or of cerium oxide, which are all photoprotective agents that are well known per se and which act by physically blocking (reflection and/or scattering) UV radiation. Standard coating agents are, moreover, alumina and/or aluminum. Depending on the particular application, sunscreens can be added to a personal care composition in amounts from 1 to 40 weight percent based on the total weight of the personal care composition, alternatively 2 to 30 weight percent on the same basis, alternatively 5 to 30 weight percent on the same basis, alternatively 15 to 30 weight percent on the same basis, alternatively 5 to 20 weight percent on the same basis.

When the composition according to the invention is an oil-in-water emulsion (o/w), it will include common ingredients generally used for preparing emulsions such as but not limited to non ionic surfactants well known in the art to prepare o/w emulsions. Examples of nonionic surfactants include polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxane surfactants.

The personal care composition can also be in the form of aqueous suspension stabilized by suspending agents and thickeners. Suspending agents include crystalline suspending agents which can be categorized as acyl derivatives, long chain amine oxides, and mixtures thereof, ethylene glycol esters of fatty acids derivatives Other suitable suspending agents include alkanol amides of fatty acids derivatives. Other suitable suspending agents include xanthan gum, carboxyvinyl polymers. Examples of these polymers include Carbopol 934, 940, 941, and 956, available from B. F. Goodrich Company. Still other suitable suspending agents include di(hydrogenated tallow)phthalic acid amide, and crosslinked maleic anhydride-methyl vinyl ether copolymer, cellulose ethers derivatives, guar gum, polyvinyl alcohol, polyvinyl pyrrolidone, hydroxypropyl guar gum, starch and starch derivatives, Suitable thickening agents are exemplified by sodium alginate, gum arabic, polyoxyethylene, guar gum, hydroxypropyl guar gum, ethoxylated alcohols, such as laureth-4 or polyethylene glycol 400.

The composition according to the invention can further contain an oil or oily component. The term oil as used herein refers to any material that is substantially insoluble in water, and which is generally compatible with any low molecular weight silicone species present in the composition. When the composition is to be used in a cosmetic or personal care product, the product components must also be cosmetically acceptable, or otherwise meet the conditions of the end use of the product.

Some examples of suitable oil components include natural oils such as coconut oil; hydrocarbons such as mineral oil and hydrogenated polyisobutene; fatty alcohols such as octyldodecanol; esters such as C12 to C15 alkyl benzoates; diesters such as propylene dipelargonate; and triesters such as glyceryl trioctanoate. Low viscosity oils can also be used such as those oils having a viscosity of 5 to 100 mPa·s at 25° C., generally consisting of esters having a structure such as RCO—OR' wherein RCO represents a carboxylic acid radical and OR' is an alcohol residue.

Some examples of low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, cocodicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol and mixtures of octyldodecanol, Caprylic/Capric triglycerides, isododecanol, soybean oil, sunflower oil, wheat and/or cereal germ oil, sweet almond oil, jojoba oil, avocado oil, olive oil, palm oil, calophyllum, and castor oil.

Other additives can include powders and pigments especially when the composition according to the invention is intended to be used for make-up. The powder component of the invention can be generally defined as dry, particulate matter having a particle size of 0.02-50 microns. The particulate matter may be colored or non-colored (for example white). Suitable powders include but not limited to bismuth oxychloride, titanated mica, fumed silica, spherical silica beads, polymethylmethacrylate beads, boron nitride, aluminum silicate, aluminum starch octenylsuccinate, bentonite, kaolin, magnesium aluminum silicate, silica, silica silylate, talc, mica, titanium dioxide, kaolin, nylon, silk powder. The above mentioned powders may be surface treated to render the particles hydrophobic in nature. The powder component also comprises various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Inorganic pigments generally consist of insoluble metallic salts of certified color additives, referred to as the Lakes or iron oxides, a pulverulent colouring agent, such as carbon black, chromium or iron oxides, ultramarines, manganese pyrophosphate, iron blue, and titanium dioxide, pearlescent agents, generally used as a mixture with colored pigments, or some organic dyes, generally used as a mixture with colored pigments and commonly used in the cosmetics industry, can be added to the composition. In general, these coloring agents can be present in an amount by weight from 0 to 20% with respect to the weight of the final composition.

Pulverulent inorganic or organic fillers can also be added, generally in an amount by weight from 0 to 40% with respect to the weight of the final composition. These pulverulent fillers can be chosen from talc, micas, kaolin, zinc or titanium oxides, calcium or magnesium carbonates, silica, colloid silica, spherical titanium dioxide, glass or ceramic beads, metal soaps derived from carboxylic acids having 8-22 carbon atoms, non-expanded synthetic polymer powders, expanded powders and powders from natural organic compounds, such as cereal starches, which may or may not be cross-linked, copolymer microspheres such as EXPANCEL (Nobel Industrie), polytrap and silicone resin microbeads (TOSPEARL from Toshiba, for example).

The waxes or wax-like materials useful in the composition according of the invention generally have a melting point range of 35 to 120° C. at atmospheric pressure. Waxes in this category include synthetic wax, ceresin, paraffin, ozokerite, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, or mixtures thereof. Mention may be made, among the waxes capable of being used as non-silicone fatty substances, of animal waxes, such as beeswax; vegetable waxes, such as carnauba, candelilla wax; mineral waxes, for example paraffin or lignite wax or microcrystalline waxes or ozokerites; synthetic waxes, including polyethylene waxes, and waxes obtained by the Fischer-Tropsch synthesis. Mention may be made, among the silicone waxes, of polymethylsiloxane alkyls, alkoxys and/or esters.

The liquid silicone resin as used in the present invention may be used in anti-perspirant and deodorant compositions in the form of, for example, sticks, soft solid, roll on, aerosol, pump spray and the like. Examples of antiperspirant agents and deodorant agents include Aluminum Chloride, Aluminum Zirconium Tetrachlorohydrex GLY, Aluminum Zirconium Tetrachlorohydrex PEG, Aluminum Chlorohydrex, Aluminum Zirconium Tetrachlorohydrex PG, Aluminum Chlorohydrex PEG, Aluminum Zirconium Trichlorohydrate, Aluminum Chlorohydrex PG, Aluminum Zirconium Trichlorohydrex GLY, Hexachlorophene, Benzalkonium Chloride, Aluminum Sesquichlorohydrate, Sodium Bicarbonate, Aluminum Sesquichlorohydrex PEG, Chlorophyllin-Copper Complex, Triclosan, Aluminum Zirconium Octachlorohydrate, or Zinc Ricinoleate, The personal care compositions of this invention may be in the form of a cream, a gel, a powder, a paste, or a freely pourable liquid. Generally, such compositions can be prepared at room temperature if no solid materials at room temperature are present in the compositions, using simple propeller mixers, Brookfield counter-rotating mixers, or homogenizing mixers. No special equipment or processing conditions are typically required. Depending on the type of form made, the method of preparation will be different, but such methods are well known in the art.

The compositions according to this invention may be applied onto a body (typically a human body) by any standard method of application. They may be applied on to skin or hair, using applicators and/or brushes or the like or by hand, by pouring and/or possibly rubbing or massaging the composition onto or into the body. Removal methods, for example for color cosmetics are also well known standard methods, including washing, wiping, peeling and the like.

For use on the skin, the compositions according to the present invention may be used in a conventional manner for example for conditioning the skin. An effective amount of the composition for the purpose is applied to the skin. Such effective amounts generally range from about 1 mg/cm$^2$ to about 3 mg/cm$^2$. Application to the skin typically includes working the composition into the skin. This method for applying to the skin comprises the steps of contacting the skin with the composition in an effective amount and then rubbing the composition into the skin. These steps can be repeated as many times as desired to achieve the desired benefit.

The use of the compositions according to the invention on hair may use a conventional manner for conditioning hair. An effective amount of the composition for conditioning hair is applied to the hair. Such effective amounts generally range from about 1 g to about 50 g, alternatively from about 1 g to about 20 g. Application to the hair typically includes working the composition through the hair such that most or all of the hair is contacted with the composition. This method for conditioning the hair comprises the steps of applying an effective amount of the hair care composition to the hair, and then working the composition through the hair. These steps can be repeated as many times as desired to achieve the desired conditioning benefit. When a high silicone content is incorporated in a hair care composition according to the invention, this may be a useful material for split end hair products.

The compositions according to this invention can be used on the skin of humans or animals for example to moisturize, color or generally improve the appearance or to apply actives, such as sunscreens, deodorants, insect repellents or the like. The recipient will notice a long lasting unique natural smooth, forming a wash off resistant film on the skin for comfort or wear and protection, easy to formulate into a broad range of personal care applications including the ones containing pigments and sunscreens and aqueous solution containing detergents such as shower gels and shampoos.

The present invention is based on the surprising effect that the inclusion of the above described liquid silicone resin results in personal care compositions with novel properties. For example, compositions containing such liquid silicone resins have better compatibility when compared to similar formulations containing other types of silicone resins known in the art. The liquid resins are especially well suited for compatibilizing linear or cyclic silicones with other organic personal care ingredients In addition, when added to a composition also containing a sunscreen agent, the liquid silicone resins provide enhanced sun protection by increasing the SPF of the composition.

EXAMPLES

The following examples are presented to further illustrate the compositions and methods of this invention, but are not to be construed as limiting the invention. All parts and percentages in the examples are on a weight basis and all measurements were obtained at room temperature (about 23° C.), unless indicated to the contrary.

As used herein:

M denotes $(CH_3)_3SiO_{1/2}$ $M^{Ph2Me}$ denotes $(C_6H_5)_2(CH_3)SiO_{1/2}$ $D^{PhMe}$ denotes $C_6H_5(CH_3)SiO_{2/2}$ $D^{Ph}{}_2$ denotes $(C_6H_5)_2SiO_{2/2}$ $T^{Pr}$ denotes $CH_3CH_2CH_2SiO_{3/2}$ $T^{Ph}$ denotes $C_6H_5SiO_{3/2}$

Examples A1-A4

Comparative A1: Preparation of Different Liquid $MT^{Pr}$ Resins

Example A1

A 12 L, 3 neck round bottom flask was loaded with DI water (4156.6 g, 230.7 mols). The flask was equipped with an air driven Teflon® stir blade on a glass stir shaft, thermometer, and a water-cooled condenser. The system was set up to capture HCl gas. An addition funnel was loaded with chlorotrimethylsilane (346.8 g, 3.192 mols), propyltrichlorosilane (1888.9 g, 10.640 mols), and n-heptane (819.07 g). Chlorosilanes were added gradually and after the addition was complete, the reaction mixture was mixed for an additional 10 minutes. The aqueous phase was then removed by draining from the bottom of the flask and adding DI water (245.7 g). Reaction mixture was heated at 80° C. for 15 minutes, and then the aqueous phase was removed. The reaction mixture was washed with an isopropyl alcohol (122.9 g):water (245.7 g) mixture. The liquid silicone resin was filtered through a 1.2 um filter under nitrogen pressure. Volatiles were removed using a rotary evaporator at an oil bath temperature of 120° C. and a vacuum of 20 mm Hg. Upon analysis using $^{29}$Si NMR, the composition of the liquid silicone resin was determined to be $M_{0.214}T^{Pr}{}_{0.786}$.

Example A2

A 5 L, 3 neck round bottom flask was loaded with DI water (882.28 g, 48.97 mols). The flask was equipped with an air driven Teflon® stir blade on a glass stir shaft, thermometer, and a water-cooled condenser. The system was set up to capture HCl gas. An addition funnel was loaded with chlorotrimethylsilane (137.51 g, 1.266 mols). The chlorosilane was added with mixing. An addition funnel was loaded with chlorotrimethylsilane (866.29 g, 7.974 mols) and propyltrichlorosilane (1118.5 g, 6.300 mols). Chlorosilanes were added slowly with vigorous mixing. After addition was complete, the reaction mixture was mixed for 1 hour at room temperature. DI water (882.28 g, 48.97 mols) was then added. Reaction mixture was heated at 80° C. for 30 minutes. Aqueous phase was then removed by draining from the bottom of the flask. DI water (244.96 g) was added. Reaction mixture was heated at 80° C. for 15 minutes, and then the aqueous phase was removed. The reaction mixture was washed with an isopropyl alcohol (122.5 g):water (245 g) mixture. The liquid silicone resin was filtered through a 0.45 um filter under nitrogen pressure. Volatiles were removed using a rotary evaporator at an oil bath temperature of 145° C. and a vacuum of 20 mm Hg. Upon analysis using $^{29}$Si NMR, the composition of the liquid silicone resin was determined to be $M_{0.536}T^{Pr}{}_{0.474}$.

Example A3

Following the procedure of Example A2 but utilizing the following quantities of reactants chlorotrimethylsilane (730.13 g, 6.72 mols), propyltrichlorosilane (1491.3 g, 8.40 mols), a liquid silicone resin with $M_{0.415}T^{Pr}{}_{0.585}$ composition (as determined by $^{29}$Si NMR) was prepared.

Example A4

Following the procedure of Example A2 but utilizing the following quantities of reactants chlorotrimethylsilane (143.40 g, 1.32 mols), propyltrichlorosilane (159.78 g, 0.90 mols), a liquid silicone resin with $M_{0.55}T^{Pr}{}_{0.45}$ composition (as determined by $^{29}$Si NMR) was prepared.

Comparative A1

Following the procedure of Example 6 of U.S. Pat. No. 6,875, 881 B2 (Kubota et al) a liquid resin with $M_{0.761}T^{Pr}{}_{0.239}$ composition (as determined by $^{29}$Si NMR) was prepared.

Examples 1-4

Comparative 1 and Control

Each of the liquid silicone resins made in Examples A1-A4 and Comparative A1 were then added to a 2% Sepigel 305 (Seppic Inc. Fairfield, N.J., USA) formulation at a 5% loading and the SPF factor quantified and compared with a control with no additive. See Table 1 for results:

TABLE 1

| Example | Additive | SPF | % SPF relative to control | Viscosity of Si resin (cSt) |
|---|---|---|---|---|
| Control | None | 5.87 | — | |
| Ex 1 | $M_{0.214}T^{Pr}{}_{0.786}$ | 42.18 | 719 | 8695 |
| Ex 2 | $M_{0.526}T^{Pr}{}_{0.474}$ | 43.08 | 734 | 40 |
| Ex 3 | $M_{0.415}T^{Pr}{}_{0.585}$ | 44.16 | 752 | 151 |
| Ex 4 | $M_{0.55}T^{Pr}{}_{0.45}$ | 42.24 | 720 | 24 |
| Comp 1 | $M_{0.761}T^{Pr}{}_{0.239}$ | 6.72 | 114 | 2 |

It is evident that the above liquid silicone resins enhance the SPF substantially beyond the control unless the end-blocker (M) content becomes too high reducing the molecular weight and viscosity to levels which compromise the SPF boost character. As the material gets to too low molecular weight (and hence viscosity) the material appears to lose its substantive film forming character and instead of helping to organize the sunscreen additives it can make them clump and lose effectiveness.

Preparation/Description of Phenyl-containing $MT^{Pr}$ liquid silicone A5-A7 and Comp A2-A9. Phenyl containing silicone fluids are commonly used in personal care products (especially color cosmetics) to provide shine characteristics (U.S. Pat. No. 6,780,402B1 and US2006/0228314 A1). The presence of the phenyl group has been shown previously to absorb light in the UV frequency region (US2004/0180011 A1).

Example A5

Following the procedure of Example A2 but utilizing the following quantities of reactants: chlorotrimethylsilane (127.06 g, 1.17 mols), propyltrichlorosilane (35.50 g, 0.200 mols), phenyltrichlorosilane (42.32 g, 0.200 mols), diphenyldichlorosilane (151.92 g, 0.600 mols), a liquid resin with $M_{0.49}D^{Ph2}{}_{0.28}T^{Pr}{}_{0.09}T^{Ph}{}_{0.14}$ composition (as determined by $^{29}$Si NMR) was prepared.

Example A6

Following the procedure of Example A2 but utilizing the following quantities of reactants: chlorotrimethylsilane (68.63 g, 0.632 mols), propyltrichlorosilane (79.89 g, 0.450 mols), phenyltrichlorosilane (57.12 g, 0.270 mols), diphenyldichlorosilane (136.73 g, 0.540 mols), a liquid resin with $M_{0.30}D^{Ph2}{}_{0.27}T^{Pr}{}_{0.24}T^{Ph}{}_{0.19}$ composition (as determined by $^{29}$Si NMR) was prepared.

Example A7

Following the procedure of Example A2 but utilizing the following quantities of reactants: chlorotrimethylsilane (1075.5 g, 9.90 mols), propyltrichlorosilane (932.1 g, 5.25 mols), diphenyldichlorosilane (379.8 g, 1.50 mols), a liquid resin with $M_{0.55}D^{Ph2}{}_{0.10}T^{Pr}{}_{0.35}$ composition (as determined by $^{29}$Si NMR) was prepared.

Comparative A2

Following the procedure of Example A2 but utilizing the following quantities of reactants: chlorotrimethylsilane (78.22 g, 0.72 mols), phenyltrichlorosilane (148.08 g, 0.70 mols), diphenyldichlorosilane (177.24 g, 0.70 mols), a liquid resin with $M_{0.30}D^{Ph}{}_{0.30}T^{Ph}{}_{0.40}$ composition (as determined by $^{29}$Si NMR) was prepared.

Comparative A3

Following the procedure of Example A2 but utilizing the following quantities of reactants: chlorotrimethylsilane (68.44 g, 0.63 mols), phenyltrichlorosilane (92.56 g, 0.438 mols), diphenylmethylchlorosilane (101.85 g, 0.438 mols), diphenyldichlorosilane (88.62 g, 0.350 mols), a liquid resin with $M_{0.31}M^{Ph2}{}_{0.20}D^{Ph2}{}_{0.20}T^{Ph}{}_{0.29}$ composition (as determined by $^{29}$Si NMR) was prepared.

Comparative A4 is a phenyl-terminated phenylmethylsiloxane fluid manufactured by Dow Corning Corporation, Midland Mich.

Comparative A5

Bisphenylpropyldimethicone A&E Connock (Perfumery & Cosmetics) Ltd, Fordingbridge, Hampshire SP6 1PU, United Kingdom.

Comparative A6

Dow Corning 200® Fluid is a 50 cSt polydimethylsiloxane fluid manufactured by Dow Corning Corporation, Midland Mich.

Comparative A7

Finsolv TN: C12-15 alkyl benzoate, Innospec Active Chemicals, LLC (Edison, N.J., USA).

Comparative A8 is Dow Corning® 217 Flake a $T^{Ph}_{1.0}$ solid flake manufactured by Dow Corning Corporation, Midland Mich.

Comparative A9

$T^{Ph}_{0.7}T^{Pr}_{0.3}$ prepared according to example 1 of U.S. Pat. No. 5,173,290.

Examples 5-7

Comparative 2-7

Each of the liquid silicone resins made in Examples A5-A7 and Comparatives A2-A7 were then added to a 2% Sepigel 305 (Seppic Inc. Fairfield, N.J., USA) formulation at a 5% loading and the SPF factor quantified. See Table 2 for results:

TABLE 2

| Ex | Additive | SPF |
|---|---|---|
| Comp 2 | $M_{0.30}D^{Ph2}_{0.30}T^{Ph}_{0.39}$ | 6.6 |
| Comp 3 | $M_{0.31}M^{Ph2}_{0.20}D^{Ph2}_{0.20}T^{Ph}_{0.31}$ | 7.2 |
| Comp 4 | Dow Corning ® PH 1555 Fluid | 8.0 |
| Comp 5 | Bisphenylpropyldimethicone | 6.1 |
| Comp 6 | Dow Corning 200 ® Fluid | 17.6 |
| Comp 7 | Finsolve TN | 8.4 |
| Comp 8 | Dow Corning ® 217 Flake | 4.5 |
| Comp 9 | $T^{Ph}_{0.7}T^{Pr}_{0.3}$ | 5.1 |
| Ex 5 | $M_{0.49}D^{Ph2}_{0.28}T^{Pr}_{0.09}T^{Ph}_{0.135}$ | 35.8 |
| Ex 6 | $M_{0.30}D^{Ph2}_{0.275}T^{Pr}_{0.24}T^{Ph}_{0.19}$ | 37.6 |
| Ex 7 | $M_{0.55}D^{Ph2}_{0.1}T^{Pr}_{0.34}$ | 29.8 |

Surprisingly, incorporating $T^{Pr}$ into phenyl containing compositions to make a liquid silicone resin was found to substantially boost the SPF value of the Sepigel formulation. Also, comparative examples 8 and 9 show that the addition of $T^{Pr}$ to solid flake materials as described in US2004/0180011 A1 have no SPF boosting character.

Example 8(a)

Use of a Liquid Silicone Resin to Compatabilize a Silicone with an Organic

Two common cosmetic ingredients, Dow Corning 200® Fluid, 350 cSt polydimethylsiloxane (pdms) fluid and glyceryl monostearate (gm) (Emerson Resources, Inc. (Norristown, Pa.) were mixed together at 10:90, 50:50, and 90:10 pdms:gm ratios by weight. All three of the mixtures were incompatible and phase separated into two distinct phases. This incompatibility can lead to issues during formulation of cosmetic products with these ingredients. To each incompatible mixture was added 10 weight percent of the fluid from example A7 and hand mixed. All three of the mixtures became clear and colorless single phase blends upon standing and remained that way for greater than one month.

Example 8(b)

Compatibility of Liquid Silicone Resins with Common Cosmetic Ingredients

The liquid silicone resins from examples A1-A4 were evaluated for compatibility with standard personal care formulating ingredients by making 1:1 blends by weight, hand mixing and observing the resulting blends for clarity and separation. The personal care formulating ingredients were isopropyl palmitate (Cognis Corporation, Care Chemicals, Ambler, Pa., USA), light mineral oil (Penreco, Karns City, Pa., USA), jojoba oil (Mountain Majestic Sage, Logan, Utah, USA) and Dow Corning 200® Fluid, 350 cSt. In all cases the blends formed homogeneous blends and with all but the highest viscosity silicone resin of example A1 the blends were crystal clear. The blends of the liquid silicone resin from Example A1 with jojoba oil, light mineral oil, and Dow Corning 200® Fluid, 350 cSt were homogeneous but all exhibited some haze.

Examples 9-14

Comparative 10 and Control 2

Use of Low Phenyl and High Phenyl Liquid Silicone Resins in Hair Shine Treatment The liquid silicone resins made in Ex A1-A4 and A7 and comp A1 were added by simple mixing to a leave-in hair treatment with the compositions shown in Table 3 and applied to the hair and measured as described in appendix 1. The measured shine values are described in Table 3.

TABLE 3

| Leave in Shine* Formulations and Results | | | | | | | | |
|---|---|---|---|---|---|---|---|---|
| | Wt % | | | | | | | |
| Example # | Ex 9 | Ex 10 | Ex 11 | Ex 12 | Ex 13 | Exm 14 | Comp 10 | Control 2 |
| Ingredients | | | | | | | | |
| Deionized Water | 96.4 | 96.4 | 96.4 | 96.4 | 96.4 | 96.4 | 96.4 | 96.4 |
| Poly-quaternium 10[1] | 0.2 | 0.2 | 0.2 | 0.2 | 0.2 | 0.2 | 0.2 | 0.2 |
| RM-2051[2] | 3 | 3 | 3 | 3 | 3 | 3 | 3 | 3 |

TABLE 3-continued

| Leave in Shine* Formulations and Results | | | | | | | | |
|---|---|---|---|---|---|---|---|---|
| | Wt % | | | | | | | |
| Example # | Ex 9 | Ex 10 | Ex 11 | Ex 12 | Ex 13 | Exm 14 | Comp 10 | Control 2 |
| Glydant DMDM Hydantoin[3] | 0.4 | 0.4 | 0.4 | 0.4 | 0.4 | 0.4 | 0.4 | 0.4 |
| Additive | 2 (Ex A1) | 2 (Ex A2 | 2 (Ex A3) | 2 (Ex A7) | 2 (Ex A5) | 2 (Ex A6) | 2 (Comp A1) | 0 |
| Shine Value | 2.90 | 2.91 | 2.79 | 2.85 | 3.08 | 3.30 | 2.19 | 2.16 |

*test method described in appendix 2
[1]Polyquaternium 10 (Amerchol Corporation, Piscataway, NJ, USA)
[2]Dow Corning ® RM-2051 Thickening Agent (Midland, MI, USA)
[3]Glydant DMDM Hydantoin (Lonza, Inc., Allendale, NJ, USA)

All of the materials of the invention provided higher shine values than the comparative and the untreated control with Ex 13 and 14 containing high phenyl content providing the highest shine enhancement.

Examples 15, 16 and Control 3

The liquid silicone resins of Ex A5 and A6 were formulated by simple mixing at 2 wt % into a serum based on ethanol, forming examples 15 and 16 respectively. These samples were then applied to hair and tested as described in Appendix 3 and compared to untreated hair and an ethanol only control (3). The shine values were measured and the results recorded in Table 4.

TABLE 4

| Serum shine results | | | | |
|---|---|---|---|---|
| | Ex 15 | Ex16 | Control 3 (Ethanol) | Untreated |
| Shine Values | 6.40 | 7.32 | 2.49 | 2.33 |
| Additive | Ex A5 | Ex A6 | — | — |

Examples 17, 18 and Control 4

The liquid silicone resins of Ex A5 and A6 were formulated by simple mixing into water-based leave-in hair conditioners as shown in Table 5 forming examples 17 and 18 respectively. These samples were then applied to hair and tested as described in Appendix 3 and compared to untreated hair and a control 4 that did not contain any silicone resin. The combing force values were measured and the results recorded in Table 6.

TABLE 5

| Water-based Leave-in hair conditioner treatment formulations | |
|---|---|
| Ingredient | Weight % |
| Emulsifying wax (Polawax)[1] | 2 |
| Behentrimonium Methosulfate (and) Cetearyl Alcohol) - Incroquat Behenyl TMS[2] | 1 |
| Deionized Water | 94.6 |
| Additive | 2 |
| Glydant DMDM Hydantoin[3] | 0.4 |

[1]Emulsifying wax (Polawax) (Croda, Inc., Edison, NJ, USA)
[2]Behentrimonium Methosulfate (and) Cetearyl Alcohol) - Incroquat Behenyl TMS (Croda, Inc., Edison, NJ, USA)
[3]Glydant DMDM Hydantoin (Lonza, Inc., Allendale, NJ, USA)

TABLE 6

| Leave-in Conditioner Comb force results | | | | |
|---|---|---|---|---|
| | Ex 17 | Ex18 | Control 4 | Untreated |
| Comb force (kg) | 0.028 | 0.034 | 0.052 | 0.038 |
| % Reduction | 26.6 | 11.6 | −32.1 | 0 |
| Additive | ExA5 | ExA6 | — | — |

From Table 6 it is apparent that adding the silicone resins of Ex A5 and A6 effectively reduce combing forces over the control and non-treated samples.

Example 19

Use of Liquid Propyl Resin in a Lotion Formulation (Skin Care)

The $M_{0.415}T^{Pr}{}_{0.585}$ material of example A3 was formulated into a lotion by mechanical mixing with a Lightnin mixer (Model L1U08F, Rochester, N.Y., USA) with the ingredients listed in Table 7. The ingredients for each of the phases were separately mixed and then the phases were mixed together. The lotion had a standard appearance with no sign of phase separation after preparation and following each of 9 freeze thaw cycles

TABLE 7

| Lotion Formulation | | |
|---|---|---|
| Ingredients | Weight % | Phase |
| Dow Corning ® HMW 2220 Non-Ionic Emulsion | 3.00% | A |
| Additive (ExA3) | 2.00% | A |
| Dow Corning 200 ® Fluid, 5 cSt | 1.20% | A |
| Polyacrylamide (and) C13-14 Isopariffin (and) Laureth-7 | 1.00% | B |

TABLE 7-continued

| Lotion Formulation | | |
|---|---|---|
| Ingredients | Weight % | Phase |
| Caprylic/Capric Triglyceride | 5.00% | B |
| Squalane (Olive Derived) | 3.00% | B |
| DI Water | 30.00% | B |
| C12-15 Alkyl Benzoate | 2.00% | B |
| DI Water | 30.00% | C |
| Dow Corning ® RM2051 Thickening Agent | 3.00% | C |
| Triethanolamine | 0.30% | C |
| Germaben II | 0.50% | D |
| Glycerin | 5.00% | D |
| Triethanolamine | 0.60% | D |
| Fragrance | 0.30% | D |
| DI Water | 13.10% | D |

Triethanolamine (BASF Corporation, Florham Park, NJ, USA)
Caprylic/Capric Triglyceride (Croda, Inc., Edison, NJ, USA)
Squalane (Olive Derived) (A&E Connock (Perfumery & Cosmetics) Ltd, Fordingbridge, Hampshire SP6 1PU, United Kingdom)
Glycerin([Jeen International Corporation, Fairfield, NJ, USA)
Polyacrylamide (and) C13-14 Isopariffin (and) Laureth-7 Germaben II (ISP Sutton, Chatham, NJ, USA)
Fragrance (Majestic Mountain Sage, Logan, UT, USA)
C12-C15 Alkyl Benzoate, (Croda, Inc., Edison, NJ, USA)

Examples 20-22

Use of Liquid Silicone Resins in Lip Gloss Formulations

The liquid silicone resins from examples A5, A6 and A7 were formulated into a lip gloss with the components described in Table 8 using a mechanical mixer (Caframo Mixer, Model BDC2002, Fisher Scientific, Pittsburgh, Pa., USA) to form Examples 20, 21 and 22 respectively.

TABLE 8

| Lip Gloss Formulations | |
|---|---|
| Ingredients | Weight % |
| Dow Corning 200 ® Fluid, 1000 cSt | 15.20% |
| Dow Corning ® 1411 Fluid | 38.00% |
| Additive | 6.30% |
| Dow Corning ® 5562 Carbinol Fluid | 12.70% |
| Dow Corning ® 593 Fluid | 7.60% |
| Dow Corning ® 9546 Silicone Elastomer Blend | 11.40% |
| Dow Corning ® HY-4008 Vegetable Oil Blend | 2.50% |
| Ethylhexyl Salicilate | 6.30% |

Ethylhexyl Salicilate (Universal Preserv-A-Chem Inc., Edison, NJ, USA)

All of the formulations showed viability with no separation following at least two freeze/thaw cycles. However, the lip gloss formulations based on the material from example A7 exhibited the greatest clarity.

Freeze/thaw Stability Cycles consists of allowing the material to be exposed to −18° C. in a freezer for at least overnight. The cups are removed from the freezer and the vials are removed from the cups and placed on the countertop to equilibrate to room temperature before making observations and recording them. Exposure to one freezing and one thawing is considered one freeze/thaw cycle.

Example 23-25

Use of Liquid Silicone Resins in a Stick Formulation

The liquid silicone resins from Ex A5-A7 were formulated to form Examples 23, 24 and 25 respectively using a mechanical mixer (Caframo Mixer, Model BDC2002, Fisher Scientific, Pittsburgh, Pa., USA) into a brown pigmented foundation stick (or lip stick) based on the formulation described in Table 9. All of the formulations produced uniform sticks which delivered the color uniformly when applied to the skin (arm).

TABLE 9

| Stick Formulation: Smooth Feel | |
|---|---|
| Ingredients | Weight % |
| Cetearyl Alcohol | 17.00% |
| Dow Corning ® 225 Fluid | 38.00% |
| Additive | 15.00% |
| Dow Corning ® HY-3050 Soy Wax | 5.00% |
| Titanium Dioxide | 16.60% |
| Talc | 5.00% |
| Iron Oxides Yellow | 2.30% |
| Iron Oxides Red | 0.90% |
| Iron Oxides Black | 0.20% |

Cetearyl Alcohol (Croda, Inc., Edison, NJ, USA)
Titanium Dioxide (A&E Connock (Perfumery & Cosmetics) Ltd, Fordingbridge, Hampshire SP6 1PU, United Kingdom)
Talc (Presperse, Inc, Somerset, NJ, USA)
Iron Oxides Yellow (Sunchemical, Yardville, NJ, USA)
Iron Oxides Red (Sunchemical, Yardville, NJ, USA)
Iron Oxides Black (Sunchemical, Yardville, NJ, USA)

Description of Test Methods

APPENDIX 1

SPF Measurement

In-Vitro SPF (Solar Protection Factor) Analysis Protocol

All materials to be analyzed for SPF level were mixed thoroughly using a Lightnin mixer set @ 1376 rpm before analysis. Each material was coated separately onto a tarred 2" by 2"×1/16" quartz plate using a 1 mil Meyer rod placed into an automatic lab drawdown machine. The coated plate must weigh between 0.058 to 0.062 g achieving 2 mg/cm$^2$ (equivalent to in-vivo method). The coated plate was dried for 20 minutes @ room temperature. It was then analyzed using a Labsphere UV 1000S Transmittance Analyzer. The coated plate was analyzed in 14 spots. If the data collected was at or below 1 A.U. (absorbance unit), the data points were averaged together and were used in the SPF calculation provided below. If the data points are above 1 A.U. a dilution is required. The dilution consisted of either a carbomer or a gelled ester that is UV transparent. The dilution data was then calculated in an Excel spreadsheet using the SPF calculation.

$$SPF = \frac{\sum_{\lambda_1}^{\lambda_2} E_\lambda S_\lambda \Delta\lambda}{\sum_{\lambda_1}^{\lambda_2} E_\lambda S_\lambda T_\lambda \Delta\lambda}$$

$E_\lambda$=CIE erythemal spectral effectiveness.

$S_\lambda$=solar spectral irradiance.

$T_\lambda$=spectral transmittance of sample.

APPENDIX 2

Hair: Leave-In Shine Test Method

Prior to treatment the tresses (International Hair Importers & Products Inc, slightly bleached (dark bleached) European hair—2 grams of hair swatched 1 inch wide, 6 inch length) were washed with 9% (active) sodium lauryl sulfate (wet each tress for 15 seconds with tap water at 40 C, using a syringe, apply 1 ml/cc of 9% active sodium lauryl sulfate, stroke through the tress for 30 seconds, rinse tress for 30 seconds under 40 C tap water, place tress on paper towel covered tray and dry overnight). Treatment procedure with leave-in conditioner—wet tress for 15 seconds under 40 C tap water, blot dry using a paper towel, apply 1.5 grams and stroke through the hair for 30 seconds, allow to dry flat on a tray overnight. The tress was combed using the wide teeth (11 teeth/25 mm) on a Unbreakable Men's Pocket Comb prior to measurement with the gloss meter. Three tresses were tested per treatment, 9 readings were taken per tress. The tresses were measured using the Gardner micro TRI-gloss meter Model 4520. The data was analyzed using Minitab Statistical Software. Individual moving range charts were used to remove any out of control points. The data set was then analyzed using an ANOVA.

APPENDIX 3

Hair: Serum Shine Test Method

Prior to treatment the tresses (International Hair Importers & Products Inc, slightly bleached (dark bleached) European hair—2 grams of hair swatched 1 inch wide, 6 inch length) were washed with 9% (active) sodium lauryl sulfate (wet each tress for 15 seconds with tap water at 40 C, using a syringe, apply 1 ml/cc of 9% active sodium lauryl sulfate, stroke through the tress for 30 seconds, rinse tress for 30 seconds under 40 C tap water, place tress on paper towel covered tray and dry overnight). Treatment procedure with serum—1000 microliters of the test solution was applied to the dry tress using a Gilson Micromen Pipet. The serum was combed through the tress 5 times with the wide teeth (11 teeth/25 mm) on an Unbreakable Men's Pocket Comb. The tress was dried using a Gold Hot 1875 Blow Dryer on the warm temperature, high speed setting. Three tresses were tested per treatment, 9 readings were taken per tress. The tresses were measured using the Gardner micro TRI-gloss meter Model 4520. The data was analyzed using Minitab Statistical Software. Individual moving range charts were used to remove any out of control points. The data set was then analyzed using an ANOVA

APPENDIX 4

Hair: Leave-in Instron

The tresses for the Instron evaluations were made from De Meo Brothers Inc. 8 inch Slightly Bleached European Hair—bleached with—2.35 to 2.5 grams of hair glued on a 2×2 inch plastic tab, after dry cut to 6 inch length) Prior to treatment the tresses were washed with 9% (active) sodium lauryl sulfate (wet each tress for 15 seconds with tap water at 40 C, using a syringe, apply 1 ml/cc of 9% active sodium lauryl sulfate, stroke through the tress for 30 seconds, rinse tress for 30 seconds under 40 C tap water, place tress on paper towel covered tray and dry overnight). Baselines were pulled prior to treatment. Treatment procedure with leave-in conditioner—wet tress for 15 seconds under 40 C tap water, blot dry using a paper towel, apply 0.3 grams and spread using finger across the length of the tress, and allow to dry flat on a tray overnight. The tresses were pulled on an Instron Model 4464. They were only pulled dry. The dry combing procedure was as follows: detangle hair by combing through by hand 3 times, retangle the hair by swirling clock wise and counter clockwise 3 times, place the tress on the hook and Instron comb, repeat the retangle and Instron combing steps five times per tress. Three tresses were pulled per treatment. The average combing load is determined (kg) for the entire length of the tress. Both Average combing load numbers and % reduction numbers were determined for the treatment (% reduction=(baseline average combing load-treatment average combing load)/baseline average combing load*100). The data was analyzed using control charts—using the within treatment variation to determine differences between treatments.

The invention claimed is:

1. A personal care composition comprising from 0.1 to 40 weight percent based on the total weight of the personal care composition of a liquid silicone resin comprising the units:

$$(PrSiO_{3/2})_m$$

$$(Me_3SiO_{1/2})_n$$

$$(PhSiO_{3/2})_o$$

$$(Ph_2SiO_{2/2})_p$$

where Pr is propyl, Me is methyl, and Ph is phenyl, m is 0.05 to 0.70, n is 0.75 to 0.20, o is 0.05 to 0.25, p is 0.05 to 0.30, m+n is from greater than 0.5 to 1, o+p is 0.05 to 0.5, n/(m+n+o+p) is at least 0.2, and m+n+o+p=1, and a cosmetic active or a health care active selected from the group consisting of an anti-acne agent, an anti-caries agent, an antidandruff agent, an antifungal agent, an antimicrobial agent, an antioxidant, an antiperspirant agent, a cosmetic biocide, a deodorant agent, an external analgesic, an oral care agent, an oral care drug, an oxidizing agent, a reducing agent, a skin bleaching agent, a skin protectant, pigments, moisturizers, vitamins, enzymes, optical brighteners, and surfactants.

2. The personal care composition of claim 1, where the personal care composition is a cosmetic product.

3. The personal care composition of claim 1, where the personal care composition is a hair care product.

4. The personal care composition of claim 1, where the personal care composition is a skin care product.

5. The personal care composition of claim 1 further comprising a sunscreen.

6. The personal care composition of claim 5, where the personal care composition is a cosmetic product.

7. The personal care composition of claim 5, where the personal care composition is a hair care product.

8. The personal care composition of claim 5, where the personal care composition is a skin care product.

* * * * *